United States Patent [19]

Miki et al.

[11] Patent Number: 4,499,880
[45] Date of Patent: Feb. 19, 1985

[54] AIR-FUEL RATIO CONTROLLING APPARATUS FOR INTERNAL COMBUSTION ENGINE

[75] Inventors: Masayuki Miki, Katsuta; Seikou Suzuki, Hitachiota; Takao Sasayama, Hitachi, all of Japan

[73] Assignee: Hitachi, Ltd., Tokyo, Japan

[21] Appl. No.: 439,878

[22] Filed: Nov. 8, 1982

[30] Foreign Application Priority Data

Nov. 11, 1981 [JP] Japan ............................... 56-179772

[51] Int. Cl.$^3$ ............................................. F02M 7/18
[52] U.S. Cl. ................................................... 123/489
[58] Field of Search ............................. 123/440, 489; 204/196 S

[56] References Cited

U.S. PATENT DOCUMENTS 4,169,440 10/1979 Taplin et al. ...................... 123/489
4,272,329 6/1981 Hetrick et al. .............. 204/196 S X
4,365,604 12/1982 Sone .................................... 123/440

FOREIGN PATENT DOCUMENTS 34058 7/1981 Japan .

Primary Examiner—Tony M. Argenbright
Attorney, Agent, or Firm—Antonelli, Terry & Wands

[57] ABSTRACT

An air-fuel ratio controlling apparatus for internal combustion engines including an oxygen sensor of hermetic type is disclosed. A pump cell of the oxygen sensor is connected with a power supply through a switch circuit for switching the direction of current flow. A control unit computes a setting of oxygen concentration of a reference gas layer of an exhaust gas sensor in accordance with the operating parameters. By a setting interruption, the control unit switches the switch circuit toward exhausting direction, drives the power supply and applies the exhaust current to the pump cell. The completion of exhaustion is detected, the switch circuit is switched to the suction, and the power supply is driven to apply the suction current to the pump cell. The setting is compared with the integration value of the suction current by a comparator circuit, or the suction current is fixed to control the drive time of the power supply. Alternatively, the current corresponding to the setting is applied for a predetermined time thereby to set the oxygen concentration of the reference gas layer to a setting in accordance with the operating parameters of the engine.

3 Claims, 7 Drawing Figures

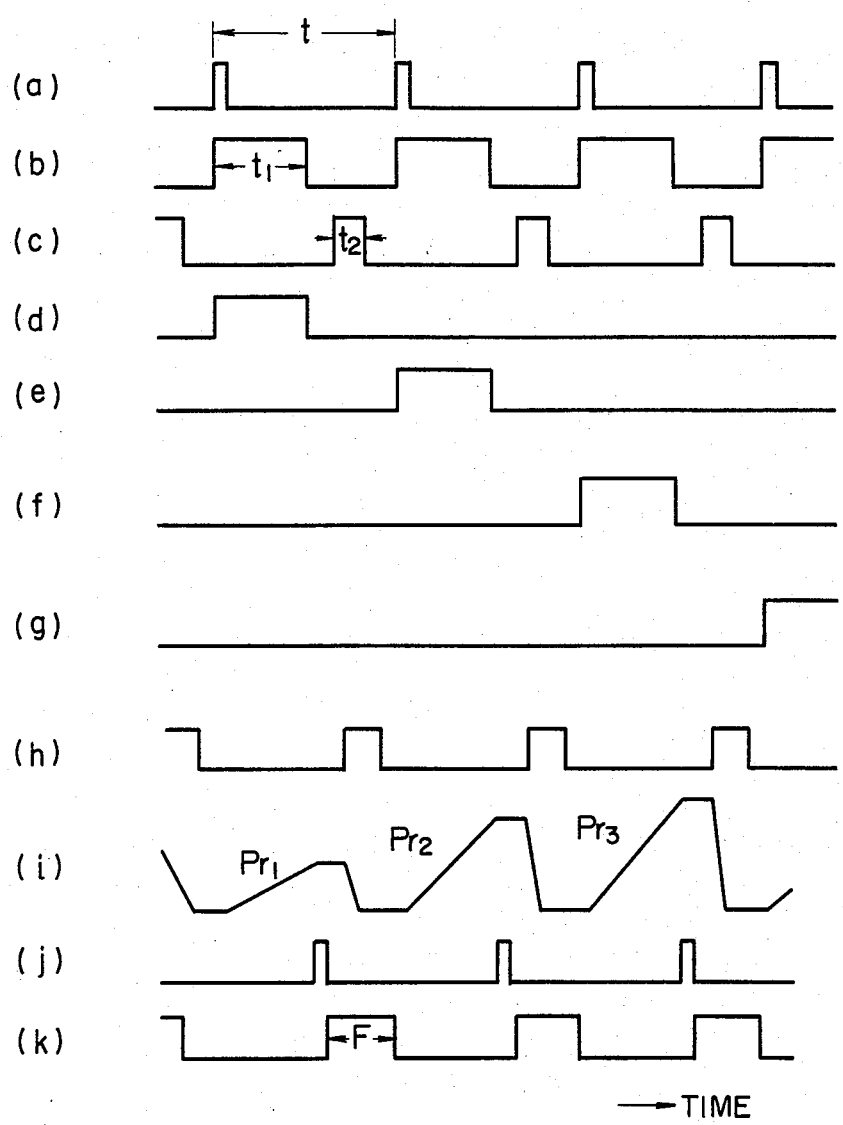

4,499,880

AIR-FUEL RATIO CONTROLLING APPARATUS FOR INTERNAL COMBUSTION ENGINE

BACKGROUND OF THE INVENTION

The present invention relates to an air-fuel ratio controlling apparatus for internal combustion engines, or more in particular to an air-fuel ratio controlling apparatus for internal combustion engines in which the amount of the current supplied to a pump cell of an exhaust gas sensor is controlled thereby to set a target air-fuel ratio at an air excess side of the stoichiometric air-fuel ratio by feedback control.

An exhaust gas sensor for detecting the oxygen in the exhaust gas is disclosed in U.S. Pat. No. 4,272,329. The exhaust gas sensor of this type requires a small aperture for introducing the exhaust gas and has the disadvantage that, when installed in the exhaust pipe, is clogged with carbon or the like, thus making accurate measurement impossible.

An exhaust gas sensor of closed type free of the above-mentioned disadvantage is disclosed in Japanese Patent Publication No. 34058/81. In this type of exhaust gas sensor, it is decided only whether or not the mixture gas is rich or lean as compared with a predetermined air-fuel ratio. This type of sensor is also such that a predetermined current continues to be supplied to a pump cell for setting the oxygen concentration of a reference gas, and therefore the detection of the oxygen concentration is likely to develop an error.

BRIEF DESCRIPTION OF THE INVENTION

An object of the present invention is to provide an air-fuel ratio controlling apparatus for internal combustion engines, in which the oxygen concentration of a reference gas layer of a sensor of closed type is capable of being accurately maintained at a set value in accordance with the operating parameters of the internal combustion engine.

According to the present invention, there is provided an air-fuel ratio controlling apparatus for internal combustion engines, comprising an exhaust gas sensor of closed type, in which the oxygen concentration of a reference gas layer of the exhaust gas sensor is set in accordance with the operating mode of the internal combustion engine.

BRIEF DESCRIPTION OF THE DRAWINGS

FIG. 5 shows a specific example circuit of the embodiment of the present invention;

FIG. 6a–6k shows a timing chart for the circuit in FIG. 5; and

DESCRIPTION OF THE PREFERRED EMBODIMENTS

Figure 1:
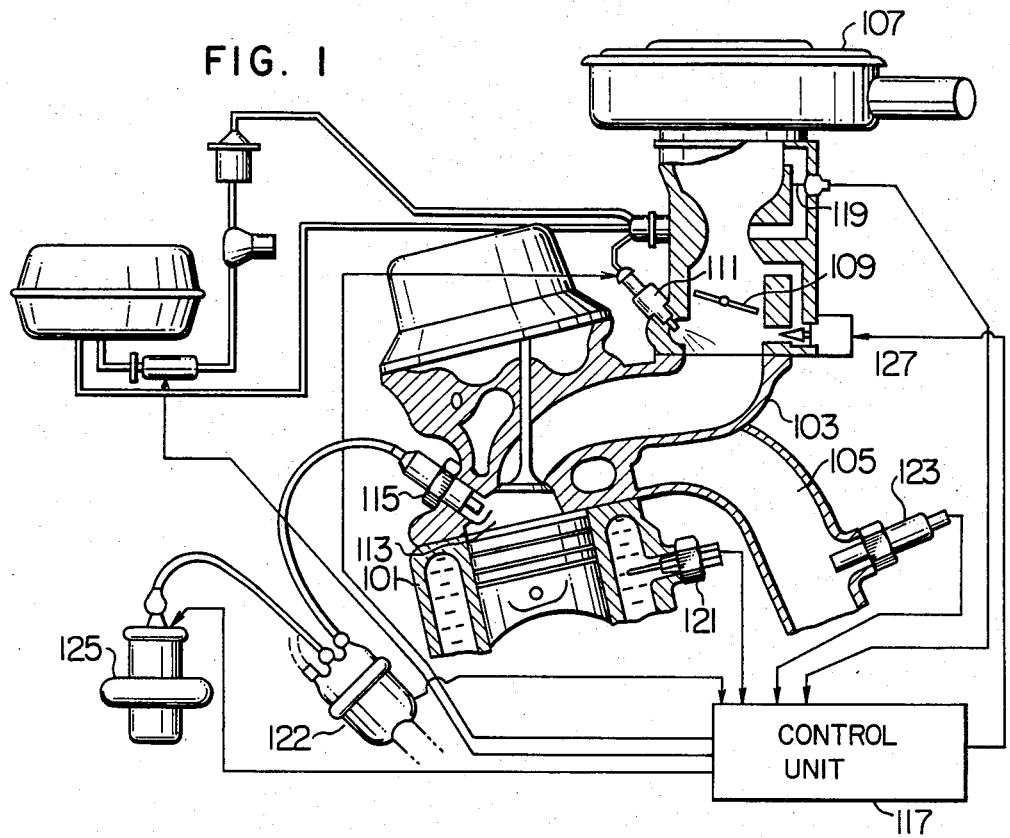
FIG. 1 shows a schematic system arrangement with various sensors and actuators for use in an engine control according to an embodiment of the present invention.

An air-fuel ratio controlling apparatus for internal combustion engines according to the present invention will be described.

An engine 101 is connected with an intake pipe 103 and an exhaust pipe 105. The air sucked through an air filter 107 is metered by a valve 109, and after being supplied with the fuel from a fuel injection valve 111 to form a mixture gas, is supplied to a cylinder 113. The mixture gas is ignited by an ignition plug 115, and after combustion, is exhausted through the exhaust pipe 105.

Figure 2:
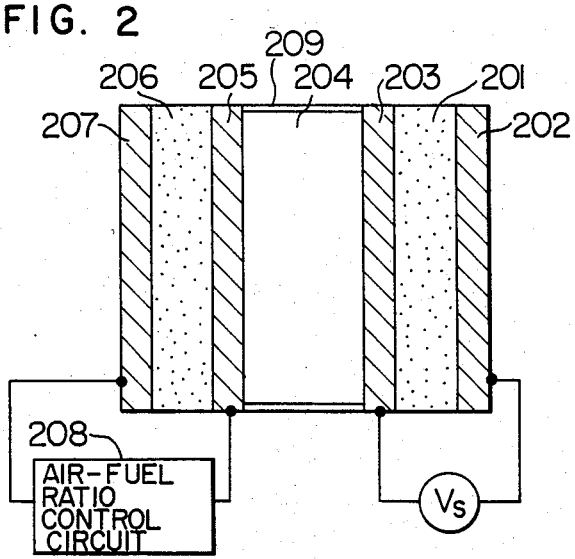
FIG. 2 is a sectional view of an exhaust gas sensor used in the embodiment of the present invention.

A control unit 117 regulates the ignition timing of the ignition signal applied to an ignition coil 125, the amount of bypass air at a bypass valve 127 and the amount of fuel injection by the fuel injection valve 111 by predetermined operation in response to outputs of an air flow sensor 119, a water temperature sensor 121, an exhaust gas sensor 123 and a crank angle sensor provided in a distributor 122. The exaust gas sensor used with the air-fuel ratio controlling apparatus will be explained with reference to FIG. 2.

A first solid electrolyte 201 of a compact sintered material is in contact, at a side thereof, with the exhaust gas through a platinum electrode layer 202 and, at the other side thereof, with a reference gas layer 204 which is hollow or made of a porous sintered material, through a platinum electrode layer 203. A second solid electrolyte 206 of the same material as the first solid electrolyte 201, which is in contact with the reference gas layer 204 through a platinum electrode layer 205, is in turn in contact with the atmosphere through a platinum electrode layer 207. The first and second solid electrolyte 201 and 206 may be made of shellac. An air-fuel ratio control circuit 208 is inserted between the platinum electrode layers 205 and 207. A voltage Vs is generated between the platinum electrode layers 202 and 203. The reference gas layer 204 is hermetically formed by the platinum electrode layers 203, 205 and a partition 209.

The platinum electrode layer 205, the second solid electrolyte 206 and the platinum electrode layer 207 make up a pump cell. The platinum electrode layer 202, the first solid electrolyte 201 and the platinum electrode layer 203 make up a sensor cell.

In the exhaust gas sensor of this construction, assume that the oxygen component pressures in the exhaust gas and the reference gas layer 204 are Pe and Pr respectively. It is known that the voltage Vs generated across the sensor cell is expressed bt Nernst's equation of (1) below.

$$V_s = \frac{RT}{4F} \cdot \ln \frac{P_e}{P_r} \quad (1)$$

where R is a gas constant, T the temperature and F Faraday's constant. The pump cell causes the oxygen component pressure in the reference gas layer 204 to change in accordance with the direction of the current flowing in the platinum electrode layers 205 and 207.

When the current Ip is supplied from the platinum electrode layer 205 to the platinum electrode layer 207 of the pump cell from the air-fuel ratio control circuit, oxygen ions move from the platinum electrode layer 207 to the platinum electrode layer 205 in the solid electrolyte 206 thereby to increase the oxygen component pressure Pr of the reference gas layer 204.

The relation between the component pressure Pr and the current Ip is given by the equation (2) below.

$$\frac{dPr}{dt} \propto K \cdot \frac{I_p}{V_R} \quad (2)$$

where K is a constant, t the time and $V_R$ the volume of the reference gas layer 204.

From the equation (2), the oxygen component pressure Pr in the reference gas layer 204 is thus expressed as $$Pr = K \cdot \frac{I_P}{V_R} t + P_o \quad (3)$$

The volume $V_R$ of the reference gas layer 204 is fixed, and therefore, if the initial value Po of the oxygen component pressure of the reference gas layer 204 is set at zero, the oxygen component pressure Pr of the reference gas layer 204 is determined by the amount of current Ip and the conduction time t. In other words, the oxygen component pressure Pr is determined by the current Ip if the time t is fixed, and determined by the time t if the current Ip is fixed.

Figure 3:
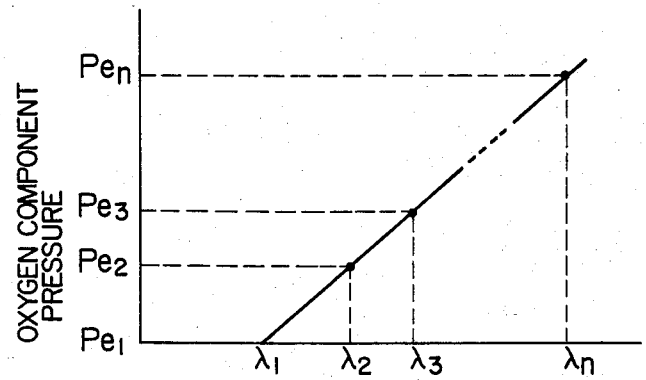
FIG. 3 is a graph showing a relationship between an air-fuel ratio λ and oxygen component pressure.

The oxygen component pressure Pr of the exahsut gas is affected by the concentration of the gas mixture supplied to the engine, namely, the air-fuel ratio λ, as shown in FIG. 3. Specifically, when λ≦1, the value of Pe is near zero, while when λ>1, Pe increases proportionately with the increases of λ. The oxygen component pressure takes the value Pe1 for $\lambda_1$, pe2 for $\lambda_2$, so on, and finally Pen for $\lambda_n$.

If the air-fuel ratio is to be controlled at a desired value λ, therefore, the current for reducing the oxygen component pressure in the reference gas layer 204 to zero is supplied to the pump cell, after which current is supplied in such an amount as to generate the oxygen component pressure Pr associated with the desired air-fuel ratio λ, so that the amount of fuel supply and the amount of air supply are controlled in a manner to reduce the voltage Vs generated across the sensor cell to zero.

Figure 4:
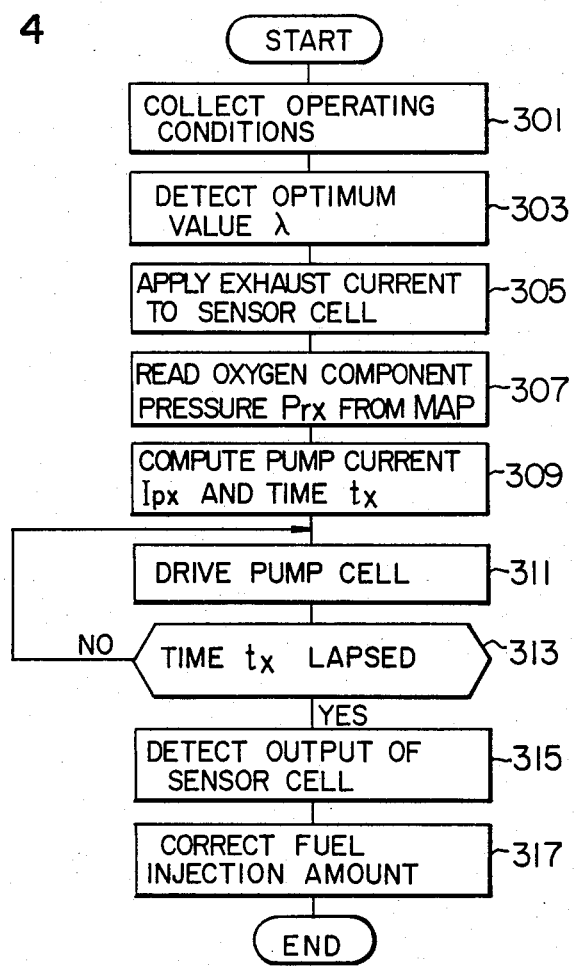
FIG. 4 is a flow chart showing the operation of a microcomputer in the embodiment of the present invention.

An air-fuel ratio controlling apparatus according to an embodiment of the present invention will be explained with the case in which the air-fuel ratio control circuit section includes a microcomputer. The flowchart for the microcomputer according to the present invention is shown in FIG. 4.

The microcomputer, which startes to operate with the start of the engine, collects the data on engine speed and intake air amount required for obtaining the optimum value λ under the present operating conditions at step 301, and then computes the desired air-fuel ratio λx from these data or detects it from the air-fuel map at step 303. At step 305, the microcomputer reduces the oxygen concentration of the reference gas layer of the exhaust gas sensor to zero in order to detect the oxygen concentration. For this purpose, a current sufficient to reduce the oxygen concentration of the reference gas layer to zero is applied to the pump cell in the exhausting direction of the pump cell.

Step 307 determines the oxygen component pressure Prx in accordance with the air-fuel ratio λx determined by step 303 from the map of FIG. 3. At step 309, the current Ipx or time tx for setting the oxygen component pressure Prx determined at step 305 is computed, followed by step 311 where the current Ipx is supplied for the predetermined time tx to the pump cell through a selection switch or the like.

After the lapse of the predetermined time tx, the output of the sensor cell is detected at step 315. At step 317, the fuel injection amount is corrected on the basis of the output of the sensor cell detected at step 315. As an example of the correction, according to the embodiment under consideration, the microcomputer detects the positive or negative state of the output of the sensor cell at step 313 from the output signal through a comparator, so that depending on whether the signal is "high" or "low", the injection pulse duration applied to the injection valve for supplying the fuel to the engine is lengthened or shortened, thereby controlling the actual air-fuel ratio to the desired value.

A specific example of hardware will be explained below with reference to FIG. 5.

The operating data including the intake air amount, water temperature and the engine speed are applied to an input-output port 523 via data input terminals 119, 121 and 124 respectively. The output of the input-output port 523 is applied to a central processing unit (CPU) 520, where the optimum air-fuel ratio λ is determined on the basis of the data stored in a random access memory 521 and a read-only memory 522, thus computing the corresponding oxygen component pressure Pr and the current Ip.

The output of the CPU 520 associated with the result of computation is applied through the input-output port 523 to a switch selector circuit 528, from which an output is sent out by way of one of the terminals $C_1$ to $C_n$ in accordance with the output of the CPU 520. The outputs of the switch selector circuit 528 are connected to switches $S_1$ to $S_n$, so that only when the output of the switch selector circuit 528 is "high", a corresponding switch is turned on. When any of the swtiches $S_1$ to $S_n$ is turned on, current is supplied to the electrode 205 of the exhaust gas sensor from a positive power supply connected with the terminal 530 through a transistor Tr1 and resistors $R_1$ to $R_n$ connected with the switches $S_1$ and $S_n$ respectively.

In view of the fact that the electrode 207 of the exhaust gas sensor is grounded and that the electrode 205 is supplied with the power supply, an electric field is generated in the solid electrolyte 206, through which the oxygen $O_2$ is injected into the reference gas layer 204. The resistance values $R_1$ to $R_n$ are in such a relation that $R_1 > R_2 > R_3 > \ldots > R_n$.

The voltage generated between the exhaust gas sensor electrodes 202 and 203 is detected by a comparator 529, the output of which is applied to the input-output port 523. According to the result of computation by the CPU 520 and the output of the comparator 529 applied to the input-output port 523, an output is supplied from the input-output port 523 to a reference signal generator circuit 527. In response to this output value, an output is applied from the terminal $D_1$ of the reference signal generator circuit 527 to the base of the transistor Tr1 for a predetermined time Tx, thus turning on the transistor Tr1 for the predetermined time Tx.

Further, the output of the terminal $D_2$ of the reference signal generator circuit 527 is applied to the base of the transistor Tr2. One end of the transistor Tr2 is connected in series to the transistor Tr1 and the other end 531 thereof to a negative power supply. The conduction time of the transistor Tr2 is controlled by the output of the reference signal generator circuit 527. As a result, an electric field opposite to the one caused by the turning on of the transistor Tr1 is generated in the solid electrolyte 206 of the exhaust gas sensor, and the oxygen is extracted from the reference gas layer 204 through the solid electrolyte 206.

In this construction, the CPU 520 is actuated with the start of the engine and in order detect the optimum air-fuel ratio λ suitable for the operating conditions, collects the operating data through the input-output port 523 from the data input terminals 119, 121 and 124 connected to external sensors or the like.

On the other hand, a plurality of air-fuel ratios λ corresponding to the operating conditions determined from the operating data is stored in the map 1 of the ROM 522, and the relation between the air-fuel ratio λ and the oxygen component pressure Pr set to the reference gas layer 504 in accordance with the ratio λ is stored beforehand in the map 2.

The CPU 520 decides the operating conditions from the operating data collected thereby and reads the optimum air-fuel ratio λ from the map 1. The oxygen component pressure Pr to be set for the reference gas layer 504 of the exhaust gas sensor corresponding to the optimum air-fuel ratio λ read from the map 1 is read from the map 2. Then, the current Ip necessary for setting the oxygen component pressure Pr for injection into or extraction from the reference gas layer 504 is computed and determined at the CPU 520 from the equation (3) above.

As obvious from equation (3) above, the oxygen component pressure Pr is proportional to the product of the current Ip and the time t. The oxygen component pressure Pr thus may be controlled either by controlling the current Ip while maintaining the time t constant or by controlling the time t while maintaining the current Ip constant. In the present case, the former method in which the current Ip is controlled while maintaining the time t fixed will be employed. The time t for injection of oxygen molecules into or time $t_2$ for extraction thereof from the reference gas layer 204 are generated by the signal generator circuit 527 from the clock signal stored in an operation control section.

Assume that the oxygen component pressure Pr1 to be set for the reference gas layer 204 and the current Ip1 for injection thereof are determined by the operation control section. An injection pulse signal having the injection time width $t_1$ is applied to the base of the transistor Tr1 from the output terminal $D_1$ of the signal generator circuit 527. This pulse is at "high" level when positive, and "low" when grounded. At the same time, the selector circuit 528, in response to the command to the operation control section, applies a signal to the control terminal of the switch from the output terminal $C_1$ corresponding to the current Ip1 among the output terminals $C_1$ to $C_n$. As a result, the current I'p determined by the switch $S_1$ turned on during the time t of "high" level of the base signal of the transistor Tr1 and the resistor $R_1$ connected with the switch $S_1$ is supplied from the electrode 205 to the electrode 207 of the pump cell, so that oxygen molecules are injected into the reference gas layer 504, thus setting the oxygen component pressure Pr1.

Assuming that the oxygen component pressure Pr2 and the current Ip2 for injecting the oxygen molecules are determined at the operation control section, the switch $S_2$ corresponding thereto is selected, so that the current determined by the resistor $R_2$ connected with the switch $S_2$ flows from a constant current source 530 to the pump cell through the transistor Tr1.

In similar manner, the switch Si corresponding to the oxygen component pressure Pri is selected and the current Ipi corresponding to the oxygen component pressure Pri is supplied to the pump cell via the resistor Ri.

When extracting the oxygen molecules from the reference gas layer 204, by contrast, an extraction pulse signal having the extraction time width $t_2$ is applied from the output terminal $D_2$ of the signal generator circuit 527 to the base of the transistor Tr2. The "high" level of this pulse signal is the earth potential and the "low" level thereof a negative potential. When the injection pulse signal is at "low" level, the "high" level of time $t_2$ is produced.

In view of the fact that the extraction of oxygen molecules is effected in order to reduce the oxygen component pressure Pr in the reference gas layer 204 to zero, the amount of current required is the one sufficient to permit the extraction of the maximum oxygen component pressure Pr set for the reference gas layer 204 during the time $t_2$. Thus unlike for the injection, a plurality of current amounts are not required for extraction, but the extraction current may be obtained from the switch Sn and the resistor Rn for obtaining the maximum current Ipn.

When an extraction pulse signal is produced, the switch Sn is turned on by the control signal produced from the output terminal Cn of the switch selector circuit in synchronism with the extraction pulse signal. The current Ip'n flows from the electrode 207 to the electrode 205 of the pump cell through the transistor Tr1 and the resistor Rn connected with the switch Sn, and also to the emitter of the transistor Tr2 through the switch Sn and the resistor Rn.

Between the electrodes 202 and 203 of the sensor cell, on the other hand, the voltage expressed by equation (1) is produced depending on the comparison between the oxygen component pressure Pe of the exhaust gas and the pressure Pr set for the reference gas layer 204, and the positive or negative state of this voltage signal is detected by the comparator 529. When the output of the comparator 529 is positive, for example, Pe is larger than Pr, and therefore the CPU 520 makes correction to shorten the injection pulse duration applied to the fuel injection valve. Conversely, when the output is negative, the injection pulse duration is lengthened. The timing of sampling the output of the sensor cell, namely, the output signal of the comparator 529 at the operation control section is taken during the holding state immediately after setting the oxygen component pressure Pr for the reference gas layer 204.

A timing chart for the circuit of FIG. 5 is shown in FIG. 6. In FIG. 6, (a) designates a clock signal stored in the CPU 20, RAM 21 and ROM 22, providing a reference signal for generating the repetition time t of the feedback control of the embodiment under consideration and also for generating a control signal for the injection and extraction current Ip thereof. (b) represents an output signal waveform produced at the output terminal $D_1$ of the reference signal generator circuit 527. During only a predetermined time when this signal is "high", the transistor Tr1 is turned on thereby to supply the injection current to the pump cell. (c) represents an output signal waveform produced at the output terminal $D_2$ of the reference signal generator circuit 527. Only during a predetermined time $t_2$ when this signal is "high", the transistor Tr2 is driven thereby to supply an exhaust current to the pump cell, thus setting the oxygen component pressure of the reference gas layer 204 to zero. (d) to (g) represent output waveforms produced at the output terminals $C_1$ to $C_4$ of the switch selector circuit respectively. (i) designates the oxygen component pressure Pr in the reference gas layer 204. The oxygen concentration Pr is changed by the current Ip, but is held when Ip is zero in a short time. (j) represents a timing signal for applying the positive and negative output signals of the sensor cell to the operation control section, so that the correction of fuel (length of the injection pulse duration) is determined by the signal thus applied. (k) represents a signal indicating the fuel correction area F in which the length of the injection pulse duration is corrected.

Assuming that the operation control section determines the oxygen concentration of the reference gas layer 204 at Pr1, an output indicated by (d) is produced at the terminal $C_1$ of the switch selector circuit thereby to turn on the switch $S_1$. Since a "high" level signal is produced at the output terminal $D_1$ of the reference signal generator circuit 527 as shown in (b), the transistor Tr1 is turned on, so that the current Ip1 is supplied to the pump cell through the transistor Tr1, the resistor $R_1$ and the switch $S_1$. As a result, the oxygen component pressure in the reference gas layer 204 slowly increases as shown in (i) and is held at Pr1 after the lapse of time $t_1$. After the lapse of time $t_1$, as shown in (j), the output of the sensor cell is sampled, and after processing operation, the fuel correction is effected within the time F shown in (k).

As shown in (h) and (c), an output is produced at the output terminal $C_n$ of the switch selector circuit and the output terminal $D_2$ of the reference signal generator circuit 527, so that the current is applied to the pump cell in the exhausting direction, thus setting the oxygen component pressure in the references gas layer 204 to zero.

In similar fashion, when the oxygen concentration in the reference gas layer 204 is determined at Pr1 by the operation control section, an output is produced at the terminal $C_2$ of the switch selector circuit as shown in (e), and as shown in (i), the oxygen component pressure in the reference gas layer 204 is set to Pr2.

As seen from above, the oxygen concentration in the reference gas layer 204 is capable of being set to a target oxygen concentration by selecting the switch selector circuit and the reference signal generator circuit.

According to the present invention, a desired oxygen component pressure is capable of being set in the reference gas layer by the current control of the pump cell. Also, by comparing it with the oxygen component pressure of the exhaust gas, the air-fuel ratio of the mixture gas supplied to the engine is optimally-controlled at a desired point in the lean region, thus improving the fuel economy and the purification of exhaust gas.

Figure 7:
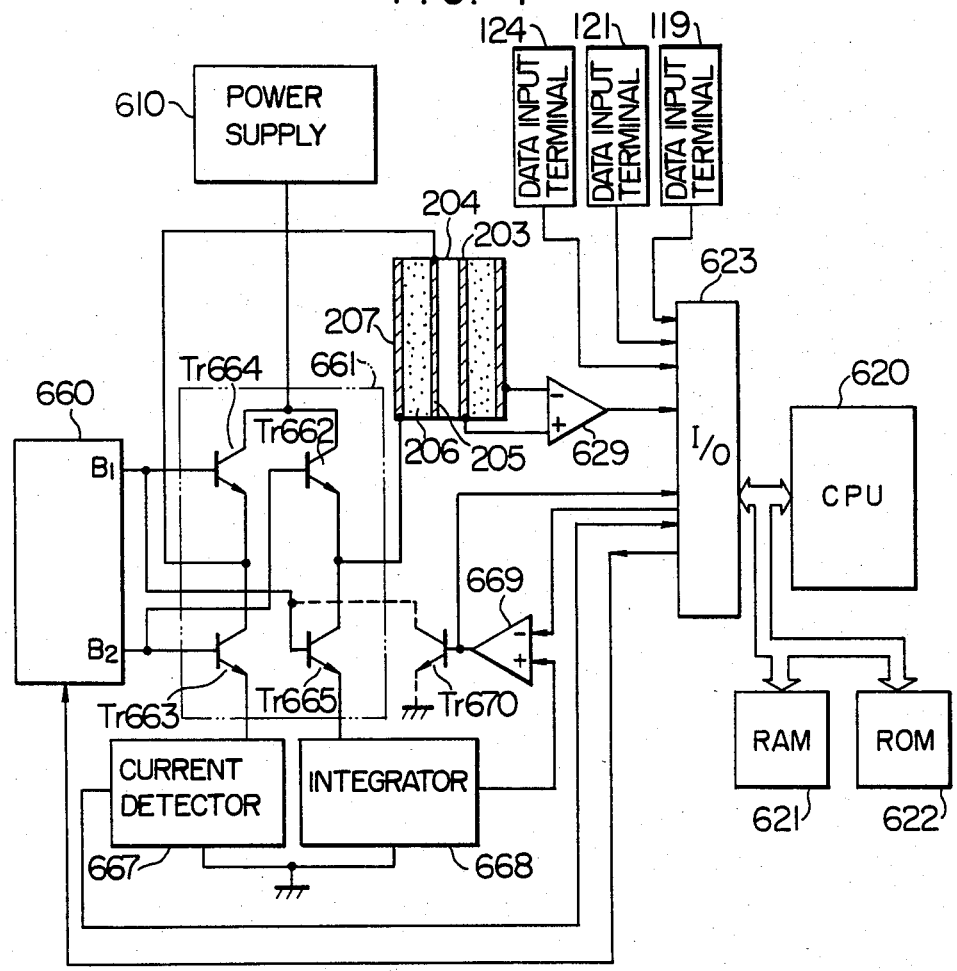
FIG. 7 is a specific example circuit in another embodiment of the present invention.

A second embodiment of the present invention will be described with reference to FIG. 7.

The operating data are applied through data input terminals 119, 121 and 124 to an input-output port 623. The output of this input-output port 623 is applied to a central processing unit 620, which decides the value of the optimum air-fuel ratio $\lambda$ on the basis of the data stored in a random access memory 621 and a read-only memory 622, and computes the oxygen component pressure Pr and the current Ip associated with the value $\lambda$.

When the central processing unit 620 decides that the time is ripe for setting the oxygen concentration of the reference gas layer of the exhaust gas sensor, a power drive circuit 660 produces a "high" signal at the terminal $B_1$ thereof, thereby turning on transistors Tr662 and Tr663 of the switch circuit 661. The pump cell is supplied with current through the power supply 610, the transistor Tr662, the electrode 207, the solid electrolyte 206', the electrode 205, the transistor Tr663 and the current detector circuit 667. When the current flows from the electrode 207 to the electrode 205 of the pump cell, the oxygen in the reference gas layer is exhausted and therefore the oxygen concentration in the reference gas layer is reduced. With the considerable decrease of oxygen concentration of the reference gas layer, the pump cell drive current determined by the amount of movement of the oxygen ions is reduced. When the current detector circuit 667 detects that the current is reduced below a predetermined level, the CPU 620 decides that the exhausting operation of the reference gas layer has been completed, and turns off the terminal $B_2$ of the power drive circuit 660 while turning on the terminal $B_1$ thereof. Then the transistors Tr664 and Tr665 of the switch circuit 661 are turned on. The current flows to the pump cell through the power source 610, the transistor Tr664, the electrode 205, the solid electrolyte 206, the electrode 207, the transistor Tr665, the integrator means 668, and the earth. The CPU 620 produces a target value of the oxygen concentration of the reference gas layer at a terminal of the comparator 669 through the input-output port 623. The output of the integrator means 668 is applied to the other terminal of the comparator 669, which in turn produces an output to the CPU when the target value is exceeded by the integrated value. When the output of the comparator 669 changes to "high" level, the central processing unit 620 is interrupted, so that the terminal $B_1$ of the power drive circuit 660 is reduced to "low" level thereby to turn off the transistors Tr664 and Tr665. In view of the delay of the processing time due to CPU which in turn causes the delay of the turn off time of the transistors Tr664 and Tr665, a transistor Tr670 as connected by dashed line in FIG. 7 may be provided in order to prevent an erroneous setting of the oxygen concentration of the reference gas layer. When the output of the comparator 669 is raised to "high" level, the transistor Tr670 is adapted to be turned on, so that the base of the transistors Tr664 and Tr665 is reduced to the grounding voltage thereby to turn off the same. In this way, the current supply to the pump cell may be cut off substantially simultaneously with the rise of the output of the comparator 669 to "high" level.

The means for setting the oxygen concentration of the reference gas layer of the exhaust gas sensor is described above. The detection of the oxygen concentration of the exhaust gas by the comparator 629, which is identical to the detection in the first embodiment, will not be explained.

It will be understood from the foregoing description that according to the second embodiment described above, the desired oxygen component pressure may be set for the reference gas layer by controlling the current of the pump cell. Also, by comparison between this desired oxygen ocmponent pressure and the oxygen component pressure of the exhaust gas, the air-fuel ratio $\lambda$ of the mixture gas supplied to the engine may be controlled optimally at a desired point in the lean area, thus improving the fuel economy and the exhaust gas purification.

Apart from the first and second embodiments described above, a constant current sourece may be provided to control the time for supplying the current from the constant current source to the pump cell.

As seen from above, according to the air-fuel ratio controlling apparatus of the present invention, the desired air-fuel ratio may be obtained without providing a special control circuit such as a delay element on the air excess side except for the stoichiometric air-fuel ratio. Especially, an optimum control value is attained meeting the demand of the engine for an improved fuel economy and exhaust gas purification.

We claim:

1. In an air-fuel ratio controlling apparatus for internal combustion engines, comprising means for supplying fuel in accordance with the operation parameters of the internal combustion engine, an exhaust gas sensor including a pump cell, a sensor cell and a reference gas layer formed hermetically between said sensor cell and said pump cell for producing an electrical output in accordance with the oxygen in the exhaust gas, and control means for controlling at least selected one of the fuel and the air supplied to the internal combustion engine in accordance with the output of said exhaust gas sensor, so that the mixture gas supplied to the internal combustion engine is controlled to a predetermined air-fuel ratio; the improvement further comprising operating mode detector means for detecting the operating mode of the internal combustion engine, and setting means for setting the oxygen concentration of said reference gas layer to a predetermined concentration in accordance with the output of said operating mode detector means, wherein said setting means includes pump cell drive means for controlling the electric charges supplied to said pump cell, said pump cell drive means including a current source and current source drive means for determining the drive time of said current source, and wherein said current source drive means includes integrator means for integrating the output of said current source, comparator means for comparing the output of said integrator means with an integration target value corresponding to a setting of the oxygen concentration of the reference gas layer, and means for cutting off said current source in accordance with the output of said comparator means.

2. In an air-fuel ratio controlling apparatus for internal combustion engines, comprising means for supplying fuel in accordance with the operation parameters of the internal combustion engine, an exhaust gas sensor including a pump cell, a sensor cell and a reference gas layer formed hermetically between said sensor cell and said pump cell for producing an electrical output in accordance with the oxygen in the exhaust gas, and control means for controlling at least selected one of the fuel and the air supplied to the internal combustion engine in accordance with the output of said exhaust gas sensor, so that the mixture gas supplied to the internal combustion engine is controlled to a predetermined air-fuel ratio; the improvement further comprising operating mode detector means for detecting the operating mode of the internal combustion engine, and setting means for setting the oxygen concentration of said reference gas layer to a predetermined concentration in accordance with the output of said operating mode detector means, wherein said setting means includes first and second power supplies for applying a voltage in the direction of suction and exhaustion of said pump cell respectively, detector means for detecting the current value supplied from said second power supply to said pump cell, and power drive means for driving said first power supply in accordance with the output of said detector means.

3. An air-fuel ratio controlling apparatus according to claim 2, wherein said first power supply is driven when said detector means detects that the current supplied from said second power supply to said pump cell is reduced to zero.

* * * * *